US006111133A

United States Patent [19]
Houlihan

[11] Patent Number: 6,111,133
[45] Date of Patent: *Aug. 29, 2000

[54] PROCESS FOR PREPARING SUBSTITUTED STYRENES

[75] Inventor: Francis Michael Houlihan, Millington, N.J.

[73] Assignee: Lucent Technologies Inc., Murray Hill, N.J.

[*] Notice: This patent issued on a continued prosecution application filed under 37 CFR 1.53(d), and is subject to the twenty year patent term provisions of 35 U.S.C. 154(a)(2).

[21] Appl. No.: 07/950,388

[22] Filed: Sep. 23, 1992

[51] Int. Cl.[7] .................. C07C 69/612; C07C 69/618
[52] U.S. Cl. ........................... 560/130; 560/150
[58] Field of Search ..................... 560/130, 150

[56] References Cited

U.S. PATENT DOCUMENTS

| | | | |
|---|---|---|---|
| 4,491,628 | 1/1985 | Ito et al. | 430/176 |
| 4,668,748 | 5/1987 | Hardam et al. | 526/240 |
| 4,689,371 | 8/1987 | Elmore | 525/374 |
| 4,996,136 | 2/1991 | Houlihan et al. | 430/313 |
| 5,082,965 | 1/1992 | Nader | 558/270 |

FOREIGN PATENT DOCUMENTS

| | | |
|---|---|---|
| 02 60 106 | 3/1988 | European Pat. Off. . |
| 0 486 267 | 11/1991 | European Pat. Off. . |

OTHER PUBLICATIONS

W.J. Dale, et al., *Journal of the American Chemical Society*, 80, 3645 (1958).
B.B. Corson, et al., *Journal of Organic Chemistry*, 23, 544 (1958).
F. Houlihan, et al., *Canadian Journal of Chemistry*, 63, 153 (1985).
H. Ito, *Journal of Polymer Science, Part A: Polymer Chemistry*, 24, 2971 (1986).
T. Kametani, et al., *Tetrahedron*, 31, 235 (1975).
H. Schmid, et al., *Helf. Chim. Acta*, 28, 722 (1945).
J.M.J. Frechet, et al., *Polymer*, 24, 995 (1983).
Piue et al., "Organic Chemistry" 4th Ed. McGraw–Hill Book Co., N.Y., p. 314–22, p. 712–15, (1980).

*Primary Examiner*—Joseph McKane
*Assistant Examiner*—Jane Oswecki
*Attorney, Agent, or Firm*—Bruce S. Schneider; Scott J. Rittman

[57] ABSTRACT

Substituted styrenes are synthesized by a simple, low temperature technique. A protected phenol styrene is reacted with an acid anhydride, dicarbonate, a halogen substituted alkyl, or an acid chloride in the presence of base to form a carbonyl substituted styrene. Unexpected yield decrease due to distillation is avoided because the product is sufficiently pure to be used without such distillation.

4 Claims, No Drawings

PROCESS FOR PREPARING SUBSTITUTED STYRENES

BACKGROUND OF THE INVENTION

1. Field of the Invention

This invention relates to synthesis of organic aromatic materials and in particular to the synthesis of substituted styrenes.

2. Art Background

Styrene materials have been used in a wide variety of applications and have found particular usefulness as monomers for the production of polymers. A class of styrene materials, styrene monomers having alkoxycarbonyloxy (ACO) substituents, have recently undergone intensive investigation as precursors to polymers employed in applications such as coatings and lithography for device manufacture. For example, t-butoxycarbonyloxystyrene co- and homo-polymers have been used in the production of polymers employed for lithographic purposes, as described in U.S. Pat. No. 4,996,136 issued Feb. 26, 1991, and U.S. patent application Ser. No. 07/806,971 filed Dec. 12, 1991 (which are hereby incorporated by reference). Additionally, 4-hydroxystyrene copolymers formed from acetoxystyrenes in the presence of base have been suggested for uses such as corrosion protection. Such polymerization is exemplified in European Patent Application A2 0260104 published Mar. 16, 1988, and U.S. Pat. No. 4,689,371 published Aug. 25, 1987, where acetoxystyrene and a second substituted styrene are reacted in the presence of base and a free radical initiator at 145° C. to form copolymers including hydroxystyrenes and other substituted styrene moieties.

Simple functionalization, e.g. esterification of the hydroxyl group in a hydroxystyrene starting material is generally very difficult due to the instability of such reactants. Therefore, styrene monomers with substituents have generally been made by first reacting materials such as di-tert-butyl dicarbonate with a hydroxyl substituted acyl-benzene such as p-hydroxybenzaldehyde to form

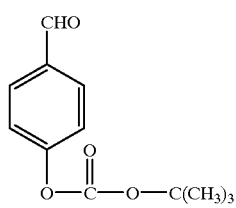

(1)

This intermediate is then reacted in the presence of a methylene Wittig reagent to form a styrene as exemplified in U.S. Pat. No. 4,491,628 Jan. 1, 1985. The process is expensive due to the cost of the Wittig reagent and due to the lower yields resulting from a multi-step procedure.

More recently, Allan E. Nader et al. have disclosed another method for synthesis of t-butoxycarbonyloxystyrene. This procedure starts from the generation of 4-hydroxystyrene using the aqueous base cleavage of 4-acetoxystyrene analogous to the same reaction of 4-vinylphenyl benzoate described by W. J. Dale et al., *Journal of the American Chemical Society*, 80, 3645 (1958), and also B. B. Corson et al., *Journal of Organic Chemistry*, 23, 544 (1958). This cleavage is followed by the phase transfer catalyzed t-butyloxycarbonylation of the phenolate derived from 4-hydroxystyrene as described by F. Houlihan et al., *Canadian Journal of Chemistry*, 63, 153 (1985). The resulting combination of steps affords high crude yields of t-butoxycarbonyloxystyrene. However, this material was, as is customary, purified by distillation and the yield of purified material after distillation is not reported.

SUMMARY OF THE INVENTION

It has been found that distillation of t-butoxycarbonyloxystyrene is problematic. Small levels of 4-hydroxyl impurities invariably present from the synthesis procedure lead to the deprotection of t-butoxycarbonyl groups and, in turn, lead to the formation of substantially higher levels of 4-hydroxystyrene impurities during distillation. This decomposition product is found in the distillate. This effect of increasing impurities by distillation occurs, it is believed, because as described by H. Ito, *Journal of Polymer Science, Part A: Polymer Chemistry*, 24, 2971, (1986), phenol moieties catalyze the thermal elimination of isobutene and carbon dioxide from the t-butoxycarbonyloxy group. Since distillation of t-butoxycarbonyloxystyrene under reduced pressure requires temperatures sufficient to cause this reaction to occur, further contamination induced during distillation substantially decreases the yield of pure product.

In the inventive process, a single reaction sequence, low temperature process has been found for producing substituted styrenes of sufficient purity that distillation is not required for most applications. Indeed, radical polymerization of the resulting styrene monomers such as 4-tert-butoxycarbonyloxystyrene and 4-methanesulfonyloxystyrene is possible without distillation of the monomer. This procedure involves the reaction of 1) a protected phenol represented by the formula:

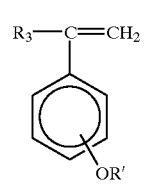

(2)

(where R' is a protecting group such as

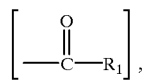

$R_3$ is not critical and is a moiety such as lower alkyl, and $R_1$ is hydrogen or a lower alkyl, e.g., 1 to 5-carbon atoms) with an aqueous base to remove the protecting group followed, without isolation, by relatively immediate reaction in the presence of base with 2) an acid halide, a halogen substituted alkyl, a dicarbonate or an acid anhydride to directly form

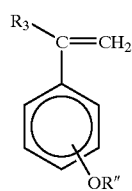

(3)

where R" is $SO_2R'''$,

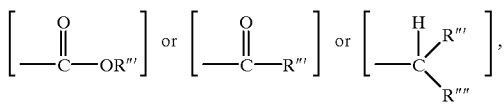

R''' is alkyl, aryl or substituted alkyl or aryl provided the substituent is not readily susceptible to undesirable base induced reactions such as hydrolysis or acid/base neutralization and R"" is R''' or H. Since the procedure occurs at room temperature in a single vessel and with relatively cheap reagents such as readily available bases, e.g. $(CH_3)_4NOH$, and since purification is not required, high yields are obtained with a simple procedure utilizing relatively inexpensive reagents. Purification is also not required to remove organic soluble phase transfer catalysts since none is employed. Additionally, since organic solvents are not employed, disposal problems are significantly reduced. Indeed, for monomers susceptible to free radical polymerization the materials are pure enough without distillation to be employed as a reactant to form polymers having a molecular weight ($M_w$) over 50,000 Daltons. This result shows a very low level of phenolic impurities in the reactant since such impurities inhibit polymerization.

DETAILED DESCRIPTION

Formation of substituted styrenes is accomplished without isolation of an intermediate by reaction of an acid anhydride, a halogen substituted alkyl, or an acid chloride with a phenolate formed from interaction of a base with the material represented by equation (2). (Other ring substituents on the material of equation (2) are not precluded provided they do not substantially interfere with the desired reaction.) Various compositions are suitable for the acid anhydride, the acid chloride or the halogen substituted alkyl. Acid anhydrides,

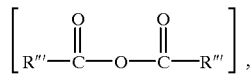

R'''=aryl or alkyl; acid halides such as X—$SO_2R'''$ or those of the formula

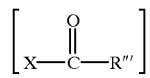

where X is a halogen; dicarbonates of the formula

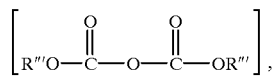

such as di-tert-butyl dicarbonate, and alkyl halides

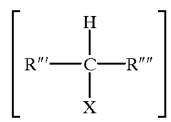

where X is a halogen are useful. The chosen reactant, however, should preferably react sufficiently slowly (or not at all) with the reaction medium, e.g. aqueous base, so that reaction with the styrene composition is not excessively limited. In case of rapid reaction, a hydrophobic solvent such as methylene chloride is advantageously used to slow the hydrolysis reaction, or in the case of extremely reactive products the intermediate hydroxystyrene is preferably isolated for reaction in an anhydrous solvent with base, and the desired reactant.

It is believed that the reaction proceeds by first inducing the formation of a phenolate through interaction of the initial reactant with two equivalents of base followed by the reaction of this intermediate (non-isolated) phenolate with the acid anhydride, acid halide, or alkyl halide. This reaction requires the formation of a bond between the oxygen of the phenoxy radical and a reactive center on the other reactant with cleavage of an existing bond to this center. (This cleavage occurs by the expulsion of what is typically called a leaving group, i.e., a group characterized by its parent acid having a $pK_a \leq 7$.) Thus, generally the reaction proceeds by interaction of the phenolate with a molecule having a leaving group.

The reaction (both hydrolysis and subsequent formation of phenolate) is induced by a base such as $(CH_3)_4NOH$, i.e. by bases having a $pK_a$ in the range 11 to 14. Although bases within this range will promote the reaction, bases such as sodium hydroxide having metal moieties should typically be avoided for electronic applications where contaminants such as sodium are quite undesirable. A stoichiometric excess of base is acceptable but this excess should be avoided if the desired product is unstable to base. However, sufficient base should be present to induce the desired degree of reaction. A control sample is easily employed to determine a suitable concentration of base for a desired efficiency of reaction.

Generally, to initiate the reaction the initial styrene reactant is introduced into the base with efficient stirring. If small quantities are being formed an addition in one aliquot is possible. However, if large quantities are being processed and heat is evolved, such addition should be controlled so that excessive temperature rise does not occur. (Generally temperatures above 35° C. induce unacceptable levels of side reactions such as polymerization.) Similarly, the acid anhydride, dicarbonate or the alkyl halide is added either with the substituted styrene or after its addition. In the former case, this second reactant should be chosen so that it does not excessively react with base to prevent substantial reaction with the styrene material. The addition of this second reactant should also be constrained so that excessive temperature rise does not occur.

The reaction is generally performed in the temperature range 5° C. to 20° C. As discussed, temperatures above 35° C. generally induce polymer formation and thus should be avoided, while temperatures below 5° C. although not precluded generally lead to a reaction rate that is inconveniently slow. Typically, the reaction is performed at atmospheric pressure, but higher pressures are not precluded. Typically, for aqueous bases further solvent is not required. However, addition of, or substitution of, non-aqueous solvents stable to both acid and base is also acceptable. It is possible to accelerate the reaction using phase transfer catalysts such as tetrabutylammonium hydroxide, but as previously discussed, this is not preferred. Use of the esters and ethers formed by the previously described reaction sequence without distillation in a radical polymerization process is possible to form polymers of weight average molecular weight greater than 50,000 Daltons.

The following examples are illustrative of the conditions employed in the inventive synthetic process.

EXAMPLE 1
Synthesis of 4-tert-Butoxycarbonyloxystyrene 10.00 gs ($6.17 \times 10^{-2}$ moles) of 4-acetoxystyrene was added to a 25 wt % solution of tetramethylammonium hydroxide (52 mL, 15% mole excess). After stirring for 15 minutes, a clear yellowish solution was obtained. To this solution was added with stirring to mix the phases 13.46 gs ($6.17 \times 10^{-2}$ moles) of di-tert-butyl dicarbonate. Slow formation of product was observed during 1 to 2 hours and the reaction essentially reached completion after 5 hours. A slight amount of residual 4-hydroxystyrene was detected by thin layer chromatography. The reaction mixture was extracted with two (15 mL) portion of ethyl ether. The ethyl ether extract was washed with 10 mL of 25% tetramethylammonium hydroxide(TMAH) and distilled water to remove base. The organic layer was dried over $MgSO_4$ filtered and the solvent removed under vacuum yielding 11.87 gs (87% yield) of pure 4-tert-butyloxycarbonyloxystyrene. Analysis of the product indicated: IR($cm^{-1}$): 2950, 1755, 1275, 1150; $^1$H NMR($CDCl_3$, ppm): 1.54(s, 9H), 5.20(d(11 Hz), 1H), 5.67(d(18 Hz), 1H), 6.67(d of d(11, 18 Hz), 1H), 7.11(d(8 Hz), 2H); 7.38(d(8Hz), 2H).

EXAMPLE 2
Synthesis of 4-tertButoxycarbonyloxystyrene

The procedure of Example I was followed except that the reagents were mixed together all at once. After workup 11.40 gs of pure product was recovered (81% yield).

EXAMPLE 3
Synthesis of 4-Methanesulfonyloxystyrene

Approximately 100 gs ($6.17 \times 10^{-1}$ moles) of 4-acetoxystyrene was added slowly to a cooled stirred solution (480 mL) of 25% TMAH (the temperature was maintained below 25° C. during the addition.) After about ½ to 1 hour of stirring, a clear, yellowish solution was obtained. This solution was cooled to 5° C. and the methanesulfonyl chloride 79.5 gs ($0.75 \times 10^{-1}$ moles) was added with stirring while the temperature was kept below 15° C through cooling with an ice bath. The reaction mixture was stirred for ½ hour until neutral pH was observed in the solution. After this time the resulting crystals were filtered-off, washed with distilled water, and sucked dry. The crystals were dissolved in a minimal amount of methylene chloride and recrystallized by addition of hexane. In this way 76 gs (62% yield) of white crystals were recovered. Analysis of the product indicated:

MP: 57–58° C.; IR(cm$^{-1}$): 2980, 1500, 1385, 1180, 1150, 980, 880, 850. $^1$H NMR($CDCl_3$, ppm): 3.14(s, 3H), 5.31(d (11 Hz), 1H), 5.74(d(18 Hz), 6.70(d of d(11, 18 Hz), 1H), 7.24(d(9 Hz), 2H), 7.44(d(9 Hz), 2H).

Elemental Analysis: Calc(C:54.53, H:5.09, S:16.17), found(C:54.35, H:5.19, S:16.22).

EXAMPLE 4
Synthesis of 4-Benzyloxystyrene

Approximately 10 gs ($6.17 \times 10^{-2}$ moles) of 4-acetoxystyrene was added to a 25 wt % solution of TMAH (51 mL). After 15 minutes of stirring a clear yellowish solution was obtained. About 10.6 gs ($6.17 \times 10^{-2}$ moles) of benzyl bromide was added to this solution with stirring. Slow formation of product crystals was observed. Reaction was complete as seen by thin layer chromatography after about 5 hours. The crystals were filtered-off, washed with distilled water, and sucked dry. In this way, 10.5 gs (81% yield) of pure desired product was obtained. Analysis of the product indicated:

MP: 68–69° C. (68–69° C., T. Kametani, et al, *Tetrahedron*, 31, 235 (1975)); IR(cm$^{-1}$): 1630, 1605, 1510, 1240, 1020, 1000, 910, 840, 700; $^1$H NMR($CDCl_3$, ppm): 4.96(s, 2H), 5.03(d(11 Hz), 1H), 5.51(d(16 Hz), 1H), 6.56(d of d(11, 16 Hz), 1H), 6.82(d(11 Hz), 2H), 7.21(d(11 Hz), 2H), 7.28(m, 5H).

Elemental Analysis: Calc(C:85.68, H:6.71), found (C:85.67, H:6.95).

EXAMPLE 5
Synthesis of 4-Vinylphenyl 4'-methylbenzoate

About 10.0 gs ($6.17 \times 10^{-2}$ moles) of 4-acetoxystyrene was added to a stirred solution (42.5 mL) of 25 wt % tetramethylammonium hydroxide. After about 15 minutes a clear yellow solution was obtained. The solution was cooled to 10 to 15° C. and p-toluoylchloride 9.54 gs ($6.17 \times 10^{-2}$ moles) was added slowly with stirring while maintaining the temperature below 25° C. During the addition, crystal formation was observed. After about ½ hour of stirring, a neutral pH was observed and the reaction reached completion as observed by thin layer chromotography. The crystals were filtered-off, washed with hexane and sucked dry. In this way, 13 gs (93% yield) of pure 4-vinylphenyl 4'-methylbenzoate was recovered. Analysis of the product indicated:

MP: 91–92° C.; IR(cm$^{-1}$): 1730, 1605, 1270, 1265, 1200, 990, 880, 750. $^1$H NMR($CDCl_3$, ppm): 2.38(s, 3H), 5.16 (d(11 Hz), 1H), 5.63(d(16 Hz), 1H), 6.64(d of d(11, 16 Hz), 1H), 7.00–7.60(m, 6H), 8.00(d(9 Hz), 2H).

Elemental Analysis: Calc(C:80.64, H:5.93), found (C:80.67, H:5.66).

EXAMPLE 6
Synthesis of 4-Ethyloxycarbonyloxystyrene

The procedure of Example I was followed except that 10.0 gs ($6.17 \times 10^{-2}$ moles) of diethyl dicarbonate was used instead of di-tert-butyl dicarbonate. The reaction was complete after 1 hour. After workup, 11.84 gs of pure product was recovered (75% yield). Analysis of the product indicated:

IR(cm$^{-1}$): 2980, 1760, 1505, 1370, 1260, 1220, 1060, 990, 900, 845, 780; $^1$H NMR($CDCl_3$, ppm): 1.36(t(8 Hz), 3H), 4.31(q(8 Hz), 4H), 5.22(d(11 Hz), 1H), 5.69(d(18 Hz, 1H), 6.68(d of d(11, 18 Hz), 1H), 7.13(d(9 Hz), 2H), 7.40(d(9 Hz), 2H).

Elemental Analysis: Calc(C:68.74, H:6.29), Found (C:68.71, H:6.40).

EXAMPLE 7
Synthesis of 4-Vinylphenyl benzoate

About 10.0 g ($6.17 \times 10^{-2}$ moles) of 4-acetoxystyrene was added to 42.5 mL of 25 wt % TMAH. After about 15 minutes of stirring in a stoppered Erlenmeyer flash, a clear yellow solution was obtained. The solution was cooled to 10° C. and 13.9 gs ($6.17 \times 10^{-2}$ moles) of benzoic anhydride was added to the stirred solution. The stirred reaction mixture was allowed to return to room temperature and the reaction reached completion after 1 hour. Workup was done by filtering-off the crystalline product, washing with distilled water and allowing the crystals to air dry. This gave 11.5 gs of pure 4-vinylphenyl benzoate (83% yield). Analysis of the product indicated:

MP: 75–76° C., (75.5–76.5° C., B. B. Corson, et al, *Journal of Organic Chemistry*, 23, 544 (1958)); IR(cm$^{-1}$): 1730, 1600, 1270, 1200, 1065, 1000, 905, 885, 705. $^1$H NMR($CDCl_3$, ppm): 5.24(d(11 Hz), 5.71(d(17 Hz), 1H), 6.71 (d of d(11, 17 Hz), 1H), 7.16(d(8 Hz), 2H), 7.42–7.60 (m, 5H), 8.19(d(8 Hz), 2H).

Elemental Analysis: Calc(C:80.34, H:5.39), found (C:80.37, H:5.55).

EXAMPLE 8

Synthesis of 4-Hydroxystyrene

About 100 g ($6.17 \times 10^{-1}$ moles) was added slowly with stirring to 42.5 mL of 25 wt % TMAH. During the addition the reaction mixture was cooled to keep the temperature below 25° C.; after about half an hour a clear yellowish solution was obtained. After cooling to 5° C., $CO_2$ was bubbled through the stirred solution until a neutral pH was obtained (about 2 hours). The crude 4-hydroxystyrene (an oil) was extracted from the aqueous mixture with about 200 mL of a ¼ mixture of ethyl acetate and petroleum ether in 50 mL aliquots. To ensure that no base was carried into the organic extract $CO_2$ was bubbled through it. This solution was dried with anhydrous $MgSO_4$, filtered, and the solvents removed under vacuum. The residue, containing small amounts of ethyl acetate was dissolved with slight heating in a minimum of petroleum ether (about 100 mL). After cooling (0° C. ) white crystals of pure 4-hydroxystyrene were obtained. After concentration of the filtrate and further crystallization a total of 67.6 gs of pure 4-hydroxystyrene was recovered (95% yield). Long term storage of this material should be done at −5 to −10° C., otherwise polymerization will ensue. Analysis of the product indicated:

MP: 68–69° C., (73.5° C., H. Schmid and P. Karrer, *Helv. Chim. Acta*, 28, 722 (1945)); $^1$H NMR($CDCl_3$, ppm): 5.12 (d(11 Hz), 1H), 5.59(d(18 Hz), 1H), 5.55(s broad, 1H), 6.63(d of d(11, 18 Hz, 1H), 6.77(d(8 Hz), 2H), 7.28(d(8 Hz), 2H).

EXAMPLE 9

Synthesis of 4-Trichloroacetoxystyrene

About 10.0 gs ($6.17 \times 10^{-2}$ moles) of 4-acetoxy styrene was dissolved in 48 mL of 25 wtw % TMAH. The solution was cooled to 5° C., and to it was added with stirring 12.6 gs ($6.95 \times 10^{-2}$ moles) of trichloroacetyl chloride. After 15 mins. of reactions, the mixture was extracted with 20 mL of methylene chloride, washed with 10 mL of TMAH solution followed by several 10 mL aliquots of water. The organic layer was dried with magnesium sulfate filtered, and the solvent removed under vacuum. In this fashion 3 gs (18% yield) of 4-trichloroacetoxystyrene was isolated. Analysis of the product indicated:

MP: 37–39° C.; IR:($cm^{-1}$):1775, 1600, 1210,850. $^1$H NMR($CDCl_3$, ppm): 5.29(d(11 Hz), 1H), 5.74(d(17 Hz), 1H), 6.70(d of d(11, 17 Hz), 1H), 7.18(d(9 Hz), 2H), 7.46(d(9 Hz), 2H).

Elemental Analysis: Calc(C:45.24, H:45.18, Cl:40.06), found(C:45.18, H:2.42, Cl:39.93).

EXAMPLE 10

Synthesis of 4-Trichloroacetoxystyrene

About 10.0 gs ($6.17 \times 10^{-2}$ moles of 4-acetoxystyrene was dissolved in 42.5 mL of 25 wt % tetramethylammonium hydroxide with stirring. The solution was cooled to 5° C. and to it was added 12.63 gs ($6.95 \times 10^{-2}$ moles) of trichloracetyl chloride dissolved in 150 mL of methylene chloride. The addition was done slowly with stirring while cooling with an ice bath so as to avoid heating the reaction mixture above 15° C. After 15 mins. of reaction, workup was done by separating the methylene chloride layer, washing it with 3×40 mL of 6 wt % tetramethylammonium hydroxide and several 40 mL aliquots of distilled water. The washed organic layer was dried over magnesium sulphate, filtered over silica gel, and the solvent removed under vacuum. The residue was recrystallized from pet ether to give 10.2 gs (62% yield) of 4-trichloroacetoxystyrene.

EXAMPLE 11

Polymerization of 4-tert-Butoxycarbonyloxystyrene 4-tert-Butoxycarbonyloxystyrene (5.00 gs, $2.27 \times 10^{-2}$ moles) and 0.03 g of AIBN were dissolved into 5 mL of dry toluene under nitrogen. This solution was freeze-thawed to remove dissolved oxygen and then heated under nitrogen at 70° C. for 12 hours. After this time, the reaction mixture was cooled, diluted with ~10 mL of methylene chloride and precipitated twice into petroleum ether, followed by washing with methanol. This gave 3.75 g of polymer (75% yield). Spectroscopic characterization confirmed that this material was poly (4tert-butoxycarbonyloxystyrene) as described previously in the literature. J. M. J. Frechet, E. Eichler, H. Ito, C. G. Willson, *Polymer*, 24, 995 (1983). Molecular weight: $M_w$, 206,000, D: 1.74.

EXAMPLE 12

Polymerization of 4-Methanesulfonyloxystyrene

4-Methanesulfonyloxystyrene (4.00 gs, $2.02 \times 10^{-2}$ moles) and 0.13 g of AIBN were dissolved into 5 mL of dry toluene under nitrogen. This solution was freeze-thawed to remove dissolved oxygen. The solution was then heated under nitrogen at 70° C. for 12 hours. After this time the reaction mixture, a tacky gum, was dissolved in 20 mL of acetone and precipitated twice into methanol. After drying, 3.2 g of polymer was recovered (80% yield). Analysis of the product indicated:

Elemental analysis: Calc(C:54.53, H:5.08, S:16.16), found(C:53.75, H:5.21, S: 15.35). $^1$H NMR($CD_2Cl_2$, ppm): 1.45–1.65(broad m, 3H), 3.10(s, 3H), 6.59(m, 2H), 7.02(m, 2H); IR:3034, 2938, 2855, 1500, 1366, 1150, 870. Molecular weight: $M_w$, 249,000; D:2.70.

What is claimed is:

1. A process for making a composition of matter, comprising the step of:

chemically reacting substituted 4-hydroxystyrene to form the composition, wherein the substituted 4-hydroxystyrene is formed by (a) treating a protected phenol with a base, and (b) interacting, in the presence of the base and in the absence of an added organic solvent, the resulting deprotected phenol with a reagent comprising a member of the group consisting of an acid halide, a halogen substituted alkyl, a dicarbonate, and an acid anhydride, wherein the chemical reaction of the substituted 4-hydroxystyrene is performed without previous distillation.

2. The process of claim 1 wherein said base comprises a tetraalkyl-ammonium hydroxide.

3. The process of claim 1 wherein said dicarbonate comprises di-tert-butyl dicarbonate.

4. The process of claim 1 wherein said acid halide comprises a compound of the formula X—$SO_2$R''' where X is a halogen and R''' is aryl or alkyl.

* * * * *